United States Patent [19]

Dobashi

[11] 4,065,484
[45] Dec. 27, 1977

[54] METHANATION PROCESS WITH INTERMITTENT REACTIVATION OF CATALYST

[75] Inventor: Harry H. Dobashi, Fullerton, Calif.

[73] Assignee: Union Oil Company of California, Los Angeles, Calif.

[21] Appl. No.: 748,134

[22] Filed: Dec. 6, 1976

Related U.S. Application Data

[63] Continuation-in-part of Ser. No. 630,977, Nov. 12, 1975, abandoned.

[51] Int. Cl.$^2$ .......................... C07C 1/04; C07C 1/16
[52] U.S. Cl. .......................... 260/449.6 M; 252/466 J
[58] Field of Search .............. 260/449.6 M, 449 M, 260/449.6 R; 252/466 J

[56] References Cited

U.S. PATENT DOCUMENTS

| | | | |
|---|---|---|---|
| 1,830,705 | 11/1931 | Marx et al. | 252/463 |
| 2,151,329 | 3/1939 | Page et al. | 260/449 M |
| 2,409,690 | 10/1946 | Nicholson et al. | 260/449.6 |
| 2,697,078 | 12/1954 | Hendel | 252/411 |
| 2,898,306 | 8/1959 | Cramer et al. | 252/463 |
| 3,147,227 | 9/1964 | Hansford | 252/437 |
| 3,320,182 | 5/1967 | Taylor et al. | 252/466 J |
| 3,361,535 | 1/1968 | Pollitzer et al. | 260/449 M |
| 3,625,665 | 12/1971 | Thompson | 260/449 M |
| 3,642,460 | 2/1972 | Thompson | 48/214 A |
| 3,709,669 | 1/1973 | Marion et al. | 260/449 M |
| 3,872,030 | 3/1975 | Feins et al. | 252/466 J |
| 3,928,000 | 12/1975 | Child et al. | 260/449 M |
| 3,958,957 | 5/1976 | Koh et al. | 260/449 M |
| 3,988,263 | 10/1976 | Hansford | 260/449 M |
| 3,999,961 | 12/1976 | White et al. | 260/449 M |

*Primary Examiner*—Howard T. Mars
*Attorney, Agent, or Firm*—Lannas S. Henderson; Richard C. Hartman; Dean Sandford

[57] ABSTRACT

A process is provided for the hydrogenation of carbon monoxide and/or carbon dioxide to form methane (methanation), using certain sulfur-sensitive nickel-alumina catalysts having a relatively low ratio of nickel surface area to nickel mass. It has been found that when such catalysts become deactivated as a result of sulfur poisoning, they can be reactivated to substantially fresh activity by reduction with hydrogen. Other nickel-alumina methanation catalysts having higher nickel surface areas are found to be essentially non-regenerable by hydrogen reduction following sulfur deactivation.

10 Claims, No Drawings

METHANATION PROCESS WITH INTERMITTENT REACTIVATION OF CATALYST

RELATED APPLICATIONS

This application is a continuation-in-part of Ser. No. 630,977, filed Nov. 12, 1975 and now abandoned.

BACKGROUND AND SUMMARY OF INVENTION

Composites of nickel and alumina are well known and widely used catalysts for the hydrogenation of carbon monoxide and/or carbon dioxide to produce methane-rich product gases. The process is generally referred to as methanation, and is highly exothermic in nature. One problem of great concern encountered in such methanation processes relates to the extreme sensitivity of nickel catalysts to poisoning by sulfur compounds, usually $H_2S$. This sensitivity has in the past necessitated the use of guard chambers to remove trace amounts of sulfur compounds from the feed gases, and/or other expensive sulfur removal processes for pretreating the feed gases. In general, in order to insure acceptable catalyst life, it is necessary to reduce the sulfur content of the feed gas to less than 1 ppm $H_2S$, and according to some authorities to less than 0.005 grains of sulfur per 1000 cubic feet of gas, which is less than 0.008 vppm (*Catalysis*, Vol. IV, Emmett ed. Reinhold Publishing Co. 1956 p.506). This problem is further aggravated by the fact that sulfur poisoning of nickel methanation catalysts has heretofore been regarded as irreversible, the sulfur-poisoned catalyst being non-regenerable. (Richardson, J. T., "SNG Catalyst Technology", *Hydrocarbon Processing*, December 1973, page 94; *Catalysis* Vol IV supra pp 504–506).

It has been firmly established that the active species of nickel for methanation is metallic nickel. The sulfur poisoning of conventional nickel methanation catalysts is attributable mainly to conversion of the active metallic nickel to inactive sulfides such as NiS. The non-regenerability of the poisoned catalysts arises because of the practical impossibility of reducing the nickel sulfide back to metallic nickel with hydrogen at temperatures below those at which sintering of the nickel occurs, i.e. below about 1500° F.

In U.S. Pat. No. 2,697,078 a nickel oxide catalyst employed for hydrodesulfurization is said to be regenerable by hydrogen reduction at 900° F, and it is speculated that in addition to removing deactivating coke deposits, the regeneration also effects the reduction: $NiS + H_2 \rightarrow Ni + H_2S$. However, as will be shown hereinafter, this reduction does not occur to any significant degree, and it must hence be concluded that the reported regeneration was due solely to the removal of deactivating coke or other deposits. It is now well established that nickel sulfide itself is very active for hydrodesulfurization.

U.S. Pat. No. 2,393,909 discloses a synthesis (Fischer-Tropsch) process utilizing a Group VIII metal catalyst, iron, cobalt and nickel being mentioned. The catalyst, after becoming deactivated by deposits of hydrocarbons, sulfur, carbon, etc. is said to be regenerable by stripping with hydrogen at undisclosed temperatures. The hydrogen is said to remove sulfur as hydrogen sulfide, and to physically or chemically strip hydrocarbonaceous materials from the catalyst. Here again, it must be presumed that any regeneration obtained was due to the removal of hydrocarbonaceous deposits and/or the hydrogenation of organic sulfur associated with such deposits, since none of the sulfides or iron, cobalt or nickel are reducible to the free metal under feasible reducing conditions. The principal and preferred catalyst disclosed for the synthesis reaction, iron, is well known to be much less sensitive to sulfur poisoning than is nickel (*Catalysis*, Vol. IV supra, p. 506).

In view of the practical irreducibility of nickel sulfide, and the established requirement for free metallic nickel in active methanation catalysts, the regeneration achieved herein is very surprising. The explanation is believed to be related to a unique characteristic of the present catalysts, which distinguishes them from prior art catalysts, namely their relatively low specific nickel surface area, ranging between about 5 and 50 $m^2/g$ of Ni. Known prior art methanation catalysts exhibit a relatively high specific nickel surface area, ranging upward from about 60 $m^2/g$ of Ni. This can only mean that a larger proportion of the nickel in the original fresh catalysts of this invention is in a catalytically inactive form, as compared to prior art catalysts.

The inactive form of nickel in the fresh catalysts utilized herein comprises at least in part, nickel aluminate, as determined by electron diffraction studies. This inactive form of nickel does not combine with sulfur, and it is postulated that during regeneration it is slowly reduced to form fresh metallic nickel, the sulfided nickel remaining in the catalyst as an inert component. This "reservoir" of inactive, non-sulfided, but recoverable nickel apparently is a distinguishing characteristic of the present catalysts. Prior art catalysts appear to be lacking in this reservoir, which could account for the fact that they regain at best only a very transient recovery of activity upon hydrogen reduction.

It should not be concluded from the foregoing that regenerability of the present catalysts is achieved only by sacrificing activity normally associated with high specific surface areas of active metal. It has been found that the methanation reaction does not require high catalytic surface areas. For catalysts containing between about 15 and 60 weight percent of Ni, very little improvement in efficiency is obtained by providing more than about 10 $m^2/g$ of nickel specific surface area. As used herein, the term "specific surface area" refers to surface area per gram of Ni, as determined by hydrogen chemisorption after reducing the fresh calcined catalyst in hydrogen for 16 hours at 700° F, as described in J.A.C.S., 86, page 2996 (1964). The actual hydrogen chemisorption is measured by the Flow method described in *J. Catalysis*, 9, page 125 (1967).

DETAILED DESCRIPTION

Catalysts having the desired characteristics of surface area, thermal stability, and regenerability required herein are best prepared by a gradual coprecipitation technique wherein basic compounds of aluminum and nickel are gradually and homogeneously coprecipitated from an aqueous solution over a period of time ranging between about 30 minutes and 24 hours or more. According to this procedure, water soluble salts, e.g. nitrates, acetates, sulfates, of aluminum and of nickel, in the proportions desired in the final catalysts, and a delayed precipitant such as urea, are dissolved in water at a relatively low temperature to provide a homogeneous solution. The proportion of urea should be sufficient to provide upon hydrolysis thereof an amount of $NH_4OH$ sufficient to precipitate all metal salts in solution as hydroxides. The solution is then heated to temperatures of e.g., 80°–110° C to effect gradual hydrolysis of urea. As hydrolysis proceeds, the urea gradually decomposes into ammonia and carbon dioxide, with resultant gradual raising of the pH of the solution. When the solution reaches about pH 4.5, some precipitation usually begins, and proceeds continuously until completed at about pH 6–7.5. It is important not to allow the pH to rise above about 8.0, for at higher pH's soluble ammonia complexes of nickel begin to form. Upon completion of coprecipitation, the coprecipitate is recovered in conventional manner as by filtration, washing and drying.

At this point it is normally desirable to shape the partially dried coprecipitate into the form desired, as by extrusion, pelleting, casting or the like. The shaped particles are then subjected to calcination at temperatures between about 700° and 1200° F for period ranging between about 1–12 hours or more. Catalysts prepared by this or other suitable delayed coprecipitation techniques, display the following herein desired characteristics:

|  | Broad Range | Preferred Range |
|---|---|---|
| Wt. % NiO (as Ni) | 15–60 | 25–50 |
| Total BET Surface Area, m²/g | 75–300 | 100–250 |
| Specific Ni Surface Area, m²/g of Ni | 5–50 | 10–35 |

Final activation of the catalyst for use in methanation is carried out, usually after the catalyst is placed in the reactor, by reduction in a flowing stream of hydrogen at temperatures of 500°–1200° F. Activation is complete when the off-gases become substantially free of water vapor.

Catalysts of the above description show outstanding utility per se in catalyzing the hydrogenation of carbon oxides to produce methane. This process is generally carried out at temperatures ranging between about 600° and 1500° F, pressures between about 100–1500 psig, and at gas hourly space velocities ranging between about 3000 and 15000 V/V/Hr. Typically, the feed gases may contain about 10–40 volume percent CO and 40–60 volume percent $H_2$, on a dry basis. The methanation reaction is extremely exothermic, and much difficulty has been encountered in controlling temperature rise in the reactor. One widely used technique under adiabatic conditions involves the recycle of large volumes of product gas (mainly methane) to serve as a heat sink, thus adding greatly to operating costs.

A less expensive approach to temperature control involves conducting the methanation in two or more adiabatic stages, with intervening cooling of the reactant gases. In the first of such stages, it would be very desirable to initiate the reaction at low temperatures of e.g. 500°–700° F and allow the exothermic temperature rise to level out at e.g. 1350°–1500° F, at which temperature equilibrium limitations substantially suppress further exothermic reaction. The exit gases are then cooled to e.g. 600°–950° F and passed into a second stage in which more favorable equilibrium peak temperatures of e.g. 1100°–1250° F are reached. Further completion of the reaction can be achieved in a third stage operating at inlet temperatures of e.g. 500°–650° F and peak temperatures of e.g. 750°–850° F. At the latter temperatures, thermodynamics permit the methanation reaction to go to 95–98% completion.

Previously available methanation catalysts do not permit of taking maximum advantage of the above multi-stage operation. At any given methanation temperature, catalyst life is a problem. Some catalysts are fairly stable at the lower temperatures, but unstable at the high temperatures. No catalyst has yet been found which can maintain its activity over the wide temperature range desired in the first stage operation described above. The only known catalysts which are sufficiently stable at temperatures above about 1100°–1200° F rapidly become inactive for low-temperature methantion, to the extent that they will not initiate the reaction at temperatures below about 1200° F. As a consequence, it has been found necessary to carry out such first-stage operations with inlet gas temperatures above 1200° F, thereby markedly decreasing efficiency. The catalysts of this invention however are found to be remarkably stable over the entire temperature range of 500°–1500° F, and may hence be employed efficiently in any of the foregoing methanation processes.

Regardless of the particular methanation technique utilized, the problem of sulfur poisoning of the catalyst is likely to arise. As noted above, rapid poisoning of the catalyst takes place unless the sulfur content of the feed gases is maintained below 1 ppm, and preferably below 0.5 ppm. Available techniques for reducing the sulfur content of typical feed gases to these low levels are very expensive and subject to periodic upset conditions, such that a considerable portion of the catalyst bed may become deactivated before desulfurization conditions can be stabilized. The regeneration technique of this invention can be conveniently utilized to reactivate catalysts deactivated as a result of feed gas desulfurization upsets, or which have purposely been allowed to deactivate in order to economize on feed desulfurization costs.

Reactivation of the sulfur poisoned catalyst is carried out by extended, high temperature reduction with a flowing stream of reduction gas consisting essentially of hydrogen, which may or may not be diluted with inert gases. Obviously, the reduction gas should be essentially completely free of sulfur compounds; no more than about 0.5 ppmv of $H_2S$ should be present. Reduction gas flow rates in the range of about 1000–10,000 GHSV will give some effective reactivation in 5 hours at temperature of 1000–1500° F. However, in most cases it will be necessary to extend the reduction time to at least about 12 hours, and sometimes up to about 200 hours for complete reactivation. Obviously, the extent to which the catalyst has been deactivated will have an important bearing on the severity and time required to achieve complete recovery of activity. In general however, operative reaction conditions can be summarized as follows:

| | Reactivation Conditions | |
|---|---|---|
| | Broad Range | Preferred Range |
| $H_2$ Flow Rate, GHSV | 1000 – 10,000 | 2000 – 8,000 |
| Temperature, ° F | 800 – 1500 | 900 – 1200 |
| Time, Hrs. | 5 – 200 | 50 – 1500 |

As will be shown hereinafter, reactivation under the above conditions converts essentially none of the nickel sulfide to metallic nickel, and removes less than 25%, usually less than about 20% of the total sulfur content as $H_2S$. However, the nickel specific surface area is substantially increased.

In most cases, the reactivation can be improved by flowing the reduction gas through the catalyst bed in an opposite direction from the previous flow of feed gases. This procedure is most effective in cases where the feed inlet portion of the catalyst bed has become more heavily sulfided than the downstream portions thereof. In this manner, any $H_2S$ generated from labile sulfur deposits on the catalyst does not contact the relatively unsulfided portion of the catalyst bed.

The following examples are cited to demonstrate effectiveness of the process, but are not to be construed as limiting in scope:

EXAMPLE 1

Catalyst Preparation

A catalyst of this invention, designated A, was prepared as follows:

About 8730 grams of $Ni(NO_3)_2 \cdot 6H_2O$ was dissolved in 15,000 ml $H_2O$, and 11,250 grams of $Al(NO_3)_3 \cdot 9H_2O$ was dissolved in 12,000 ml $H_2O$ to which another 3000 ml of $H_2O$ was added after mixing the two salt solutions in a 25-gallon steam-jacketed stainless-steel kettle equipped with stirrer and thermometer. A third solution consisting of 4800 grams of urea in 15,000 ml $H_2O$ was then added to the kettle. The total volume of solution in the kettle was about 15.4 gallons.

The solution was heated by introducing 15 pound steam into the kettle jacket. Vigorous stirring was used to obtain rapid heat transfer; heat-up to 209° F required about 1 hour. At this temperature, rapid evolution of $CO_2$ occurred due to urea hydrolysis. After about four hours at 209°–210° F the pH had risen from about 2.3 to 4.5, at which point some precipitation had started. Urea hydrolysis was allowed to continue, the pH rising to 5.3 in 85 more minutes where it remained for about two hours before slowly rising to about 6.0 during the next 2.5 hours. The slurry was then allowed to cool overnight before discharge from the kettle and filtering.

A sample of filtrate was analyzed for nickel by X-ray fluorescence and found to contain 3.6 mg Ni/ml. Since a total of 29 liters of filtrate was collected, 104.4 grams of nickel out of 1750 grams taken had not precipitated, or about 6% of the total. A sample of filtrate was heated at 95° C for another 24 hours and further precipitation occurred. This shows that loss of nickel can be substantially eliminated by longer digestion time or by using slightly more urea, so that the final pH is close to 7 (but below about pH 8, where soluble ammonia complexes begin to form).

After a final water wash, the filter cake was dried at 250° F to an LOI of 32.2%. It was ground to a fine powder in a hammer mill, dry-ground in a muller for 2 hours, then wet-mulled to an extrudable paste. The paste was then extruded through a 1/16 inch die, air dried, and calcined at 900° F for 3 hours. The finished catalyst contained 44% Ni and had a total surface area of 184 m$^2$/g.

After reducing for 16 hours at 700° F in 100% $H_2$ as described in *J.A.C.S.* 86 p. 2996 (1964), the catalyst was found to have a nickel specific surface area of 18.9 m$^2$/g of Ni, as measured by the Flow method described in *J. Catalysis*, 9, p. 125 (1967).

EXAMPLE 2

Activity Testing

Catalyst A of Example 1 was tested for methanation activity, along with a comparison Catalyst B. Catalyst B was a commercial Ni—$Al_2O_3$ methanation catalyst prepared by conventional, rapid coprecipitation, containing about 45–50 wt.% Ni, and having a nickel specific surface area of about 70–80 m$^2$/g of Ni. The conditions of the test procedure were as follows:

| Feed Gas Composition: | |
|---|---|
| $H_2$ | 30.9 vol.% |
| $CH_4$ | 9.6 |
| CO | 7.9 |
| $CO_2$ | 7.9 |
| $H_2O$ | 43.7 |
| Inlet Temperature | 900° F |
| Outlet Temperature | 1220° F (Calculated Adiabatic) |
| Pressure | 300 psig |
| Catalyst Volume | 85 ml (13" bed length) |
| GHSV | 10,000 |

Since the reactor was heated in a fluidized sand bath, reaction conditions were not adiabatic, but quasi-isothermal. Typically, the peak temperatures were 1150°–1175° F, dropping to about 925° F at the outlet as a result of cooling by the sand bath. The equilibrium composition established at the lower temperature corresponds to approximately 98% conversion of CO.

Seven thermocouples were placed in the upper portion of the catalyst bed, the first about ½ inch below the top of the bed, and the remainder spaced about ½ inch apart down the bed. By this arrangement the catalyst deactivation rate can be observed as the peak temperature travels slowly down the bed, reflecting progressive catalyst deactivation. Also, the difference in temperature (ΔT) between successive thermocouples reflects the amount of reaction occurring over the respective intervals between thermocouples. A negative ΔT indicates that the reaction has already gone essentially to equilibrium, permitting cooling by the sand bath to take place. At the end of 6 days, the respective temperatures were as follows:

TABLE I

| | Temperatures Prior to Introduction of $H_2S$, ° F | | | |
|---|---|---|---|---|
| | Feed Inlet 900° F | | ΔT from Feed Inlet or from Preceding Thermocouple, ° F | |
| Thermocouple | Cat A | Cat B | Cat A | Cat B |
| 1 | 1145 | 1155 | 245 | 255 |
| 2 | 1155 | 1150 | 10 | −5 |
| 3 | 1135 | 1125 | −20 | −25 |
| 4 | 1120 | 1112 | −15 | −13 |
| 5 | 1102 | 1090 | −18 | −22 |
| 6 | 1080 | 1072 | −22 | −18 |
| 7 | 1060 | 1052 | −20 | −20 |

The foregoing shows that, in the absence of sulfur, each catalyst was highly active after 6 days, nearly all of the reaction taking place in the first ½ inch of catalyst bed.

EXAMPLE 3

Sulfur Deactivation

At the end of the 6-day run of Example 2, the feed gas was modified by adding thereto 4 ppmv of $H_2S$. After 17 hours, the respective temperatures were as follows:

TABLE 2

| | Temperatures 17 Hrs After Introduction of 4 ppm $H_2S$, ° F | | | |
|---|---|---|---|---|
| | Feed Inlet 900° F | | ΔT From Feed Inlet or From Preceding Thermocouple, ° F | |
| Thermocouple | Cat A | Cat B | Cat A | Cat B |
| 1 | 900 | 900 | zero | zero |
| 2 | " | " | " | " |
| 3 | " | " | " | " |
| 4 | " | " | " | " |

TABLE 2-continued

| Thermocouple | Temperatures 17 Hrs After Introduction of 4 ppm H$_2$S, °F | | | |
|---|---|---|---|---|
| | Feed Inlet 900° F | | ΔT From Feed Inlet or From Preceding Thermocouple, °F | |
| | Cat A | Cat B | Cat A | Cat B |
| 5 | " | " | " | " |
| 6 | " | 915 | " | 15 |
| 7 | 905 | 945 | 5 | 30 |

It is evident from the foregoing that substantially the entire portion of the catalyst bed in which the thermocouples were embedded had become deactivated.

EXAMPLE 4

Catalyst Reactivation

Following the sulfur deactivation of Example 3, each catalyst was reduced in a stream of hydrogen at 6660 GHSV for about 17 hours at 900° F, and 85–89 hours at 1100° F. Following this, methanation was resumed under the conditions of Example 2, with the following results:

TABLE 3

| Thermocouple | Temperatures Immediately After Regeneration, °F | | | |
|---|---|---|---|---|
| | Feed Inlet 900° F | | ΔT From Feed Inlet or From Preceding Thermocouple, °F | |
| | Cat A | Cat B | Cat A | Cat B |
| 1 | 1085 | 1060 | 185 | 160 |
| 2 | 1115 | 1115 | 30 | 55 |
| 3 | 1130 | 1125 | 15 | 10 |
| 4 | 1130 | 1130 | 0 | 5 |
| 5 | 1115 | 1115 | −15 | −15 |
| 6 | 1100 | 1100 | −15 | −15 |
| 7 | 1085 | 1085 | −15 | −15 |

From the foregoing, it is evident that the initial activity of each of the regenerated catalysts was quite similar, approaching that of the respective fresh catalysts.

EXAMPLE 5

Regenerated Catalyst Stability

Methanation in the absence of H$_2$S was continued as in Example 4 for an additional 6 days. At the end of the 6-day period the temperatures were as follows:

TABLE 4

| Thermocouple | Temperatures 6 Days After Regeneration, °F | | | |
|---|---|---|---|---|
| | Feed Inlet 900° F | | ΔT From Feed Inlet or From Preceding Thermocouple, °F | |
| | Cat A | Cat B | Cat A | Cat B |
| 1 | 1000 | 915 | 100 | 15 |
| 2 | 1085 | 975 | 85 | 60 |
| 3 | 1115 | 1062 | 30 | 87 |
| 4 | 1137 | 1135 | 22 | 73 |
| 5 | 1125 | 1145 | −12 | 10 |
| 6 | 1110 | 1135 | −15 | −10 |
| 7 | 1090 | 1120 | −20 | −15 |

From the foregoing temperatures at thermocouple 1, it is evident that the top portion of catalyst bed B was almost completely deactivated after 6 days, while the corresponding portion of catalyst bed A still retained about 54% of the freshly regenerated activity shown in Table 3. At 46% deactivation per 6-day period, another 18 days, or a total of 24 days, would be required for catalyst A to reach the same state of deactivation which catalyst B reached in 6 days. It is thus evident that regenerated catalyst A is at least four times as stable as regenerated catalyst B.

The foregoing is however a conservative estimate because thermal deactivation of catalysts is not a simple arithmetic progression unless all active sites in the catalyst have the same activity and stability, which is not the usual case. A more realistic estimate would rank regenerated catalyst A as being about six times as stable as regenerated catalyst B, since after 6 days the upper portion thereof was only about one-sixth as active as the corresponding portion of catalyst A, as reflected by the ΔT values at the first thermocouple. Also, during the 6-day post-regeneration run, thermocouple 1 of catalyst B registered 1000° F after only 1 day, whereas thermocouple 1 of catalyst A did not decline to that temperature until 6 days had elapsed.

EXAMPLE 6

Sulfur Loss During Regeneration

Two samples of a catalyst essentially identical to catalyst A of the foregoing examples, which catalyst had been deactivated by sulfur deposition during methanation, were analyzed for sulfur content. One sample analyzed 0.22 weight-percent and the other 0.23 weight-percent of total sulfur. These low sulfur contents clearly reflect the fact that only a very minor portion of the total nickel content had been sulfided; yet the catalyst was almost completely inactive, having a very low specific surface area of Ni.

An 85 ml sample of the deactivated catalyst, in the form of 8–10 mesh particles was loaded into an elongated reactor and hydrogen, flowing at the rate of 20 SCF/hr., was passed through the catalyst bed at 900° F for 22 hours. The temperature was then raised to 1100° F over a period of 2 hours, and the flow of hydrogen was continued at 1100° F for an additional 82 hours. This regeneration treatment is essentially identical to that utilized in Example 4.

Following the reduction treatment, two samples of the catalyst were analyzed for sulfur content. The first sample was taken from the top 10% of the catalyst bed, while the second sample was a homogeneous composite taken from the lower (downstream) 90% of the bed. Both samples analyzed 0.19 wt.% total sulfur. The fact that, after 106 hours of hydrogen stripping, the upstream and downstream portions of the catalyst bed had identical sulfur contents clearly demonstrates that no sulfur was being removed at 106 hours, and also that the small amount of sulfur which had been removed must have been a different, labile form than the sulfur remaining. Despite the insignificant sulfur removal, the catalyst displays stable activity, as demonstrated in Example 5.

The following claims and their obvious equivalents are believed to define the true scope of the invention:

I claim:
1. A methanation process wherein:
   1. a stream of contaminated feed gas comprising hydrogen and carbon monoxide and/or carbon dioxide is contacted with a nickel-alumina catalyst at temperatures between about 600° and 1500° F to produce methane;
   2. said catalyst has a total nickel content between about 15 and 60% by weight, calculated as Ni, one portion of said nickel content being in an active metallic state, and another portion thereof being nickel aluminate, the nickel specific surface area of said catalyst in its freshly reduced state being between about 5 and 50 m²/gm of Ni;
3. said feed gas is contaminated with H₂S or a sulfur compound which yields H₂S upon hydrogenation, whereby said catalyst becomes at least partially deactivated;
4. said deactivated catalyst is reactivated with essentially no removal of sulfur therefrom by contacting the same with a substantially sulfur-free stream of reactivating gas consisting essentially of hydrogen, said reactivation contacting being carried out at between about 800° and 1500° F and continued for at least about 5 hours; and
5. the resulting reactivated catalyst is again placed on-stream for methanation as defined in (1) above.

2. A process as defined in claim 1 wherein said reactivation contacting is continued for at least about 12 hours.

3. A process as defined in claim 1 wherein said stream of reactivating gas contacts said catalyst in an opposite flow direction from the flow direction of said feed gas stream.

4. A process as defined in claim 1 wherein said catalyst is prepared by the steps of:
 1. forming at a relatively low temperature a homogeneous aqueous solution of an aluminum salt, a nickel salt and urea;
 2. heating said aqueous solution to a sufficiently high temperature to bring about hydrolysis of said urea with resultant gradual increase in pH of said solution and formation of a coprecipitate of basic compounds of nickel and aluminum;
 3. separating said coprecipitate from said solution before the latter reaches a pH above about 8; and
 4. drying and calcining said coprecipitate.

5. A process as defined in claim 4 wherein said catalyst contains between about 25 and 50% by weight of nickel, calculated as Ni.

6. A process as defined in claim 4 wherein the nickel specific surface area of said catalyst is between about 10 and 35 m²/g of Ni.

7. A methanation process wherein:
 1. a stream of contaminated feed gas comprising hydrogen and carbon monoxide and/or carbon dioxide is contacted with a nickel-alumina catalyst at temperatures between about 600° and 1500° F to produce methane;
 2. said catalyst has a total nickel content between about 25 and 50% by weight, calculated as Ni, one portion of said nickel content being in an active metallic state, and another portion thereof being nickel aluminate, the nickel specific surface area of said catalyst in its freshly reduced state being between about 10 and 35 m²/gm of Ni;
 3. said feed gas is contaminated with H₂S or a sulfur compound which yields H₂S upon hydrogenation, whereby said catalyst becomes at least partially deactivated;
 4. said deactivated catalyst is reactivated with essentially no removal of sulfur therefrom by contacting the same with a substantially sulfur-free stream of reactivating gas consisting essentially of hydrogen, said reactivation contacting being carried out at between about 800° and 1500° F and continued for at least about 5 hours; and
 5. the resulting catalyst is again placed on-stream for methanation as defined in (1) above.

8. A process as defined in claim 7 wherein said reactivation contacting is continued for at least about 50 hours.

9. A process as defined in claim 7 wherein said stream of reactivating gas contacts said catalyst in an opposite flow direction from the flow direction of said feed gas stream.

10. A process as defined in claim 7 wherein said catalyst is prepared by the steps of:
 1. forming at a relatively low temperature a homogeneous aqueous solution of an aluminum salt, a nickel salt and urea;
 2. heating said aqueous solution to a sufficiently high temperature to bring about hydrolysis of said urea with resultant gradual increase in pH of said solution and formation of a coprecipitate of basic compounds of nickel and aluminum;
 3. separating said coprecipitate from said solution before the latter reaches a pH above about 8; and
 4. drying and calcining said coprecipitate.

* * * * *